Figure 1:
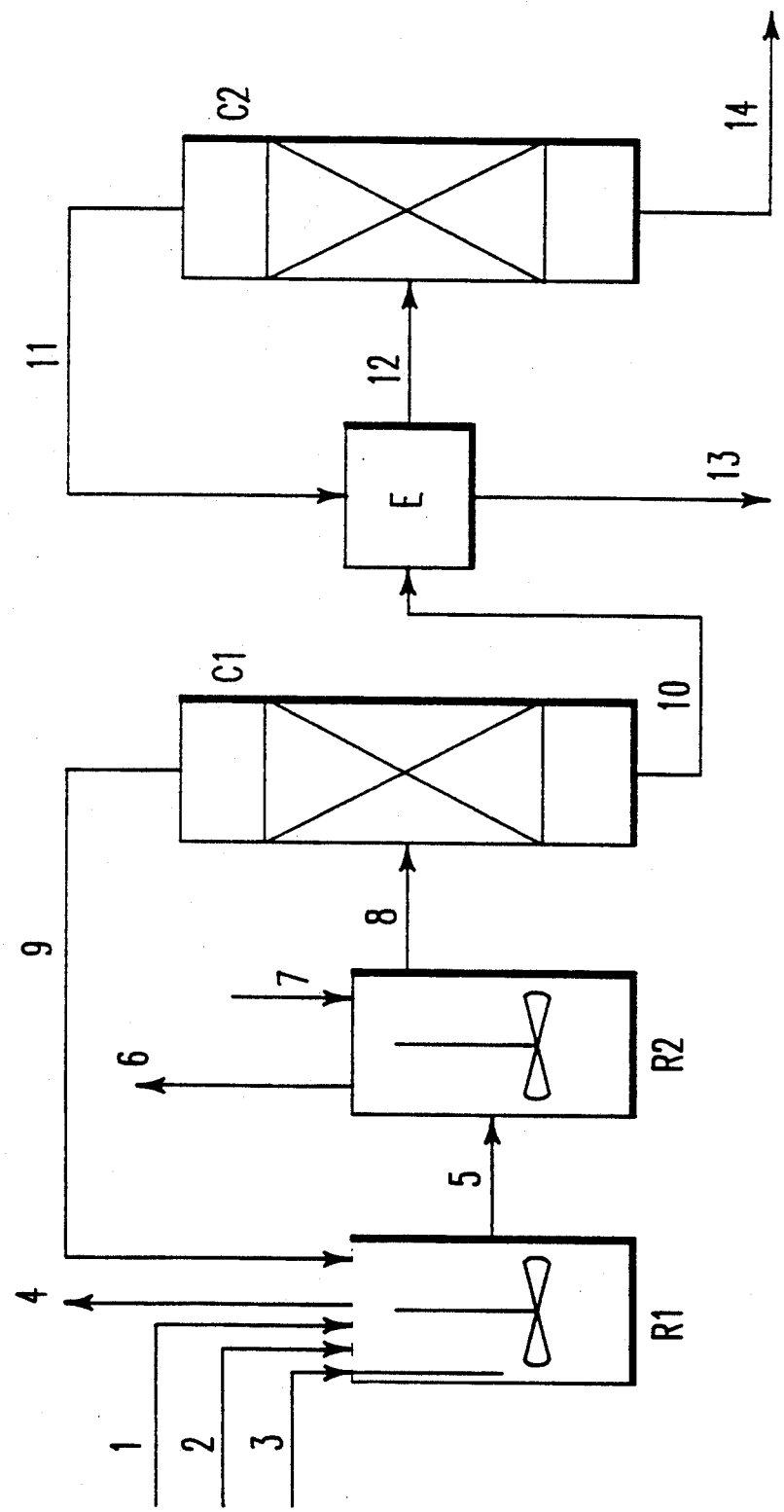

United States Patent [19]
Tonti et al.

[11] Patent Number: 5,227,525
[45] Date of Patent: Jul. 13, 1993

[54] MULTISTEP PROCESS FOR THE LIQUID PHASE AMMOXIMATION OF CARBONYL COMPOUNDS

[75] Inventors: Sergio Tonti, Venice; Paolo Roffia, Varese; Vittorio Gervasutti, Venice, all of Italy

[73] Assignee: Enichem Anic s.r.l., Palermo, Italy

[21] Appl. No.: 822,907

[22] Filed: Jan. 21, 1992

[30] Foreign Application Priority Data

Jan. 23, 1991 [IT] Italy .................. 91 A/000144

[51] Int. Cl.$^5$ .................................. C07C 249/04
[52] U.S. Cl. .................... 564/267; 564/253; 564/259; 564/265; 564/268
[58] Field of Search ............ 564/253, 259, 265, 267, 564/268

[56] References Cited

U.S. PATENT DOCUMENTS

| | | | |
|---|---|---|---|
| 4,745,221 | 5/1988 | Roffia et al. | 564/267 |
| 4,794,198 | 12/1988 | Roffia et al. | 564/267 |
| 4,894,478 | 1/1990 | Roffia et al. | 564/267 |
| 4,968,842 | 11/1990 | Padovan et al. | 564/253 |
| 5,014,652 | 8/1991 | Padovan et al. | 564/267 |

*Primary Examiner*—Richard L. Raymond
*Attorney, Agent, or Firm*—Oblon, Spivak, McClelland, Maier & Neustadt

[57] ABSTRACT

A multistep process for the liquid phase ammoximation of carbonyl compounds with $H_2O_2$ and $NH_3$, at 60°-100° C., at 1.5-5 bar and in the presence of a catalyst based on silicon, titanium and oxygen, characterized in that:

a) in one or more primary steps, the $H_2O_2$: carbonyl compound molar ratio ranges from 0.9 to 1.15 by mols and the carbonyl component conversion is carried out up to at least 95%;

b) in a last (exhaustion) step the $H_2O_2$: carbonyl compound ratio is in a higher range, i.e. from 1.5 to 3.0 by mols.

17 Claims, 4 Drawing Sheets

MULTISTEP PROCESS FOR THE LIQUID PHASE AMMOXIMATION OF CARBONYL COMPOUNDS

The invention relates to a multistep process for the liquid phase ammoximation of carbonyl compounds with hydrogen peroxide and ammonia. A typical example is the ammoximation of cyclohexanone to cyclohexanone-oxime, and in the text reference will be almost always made to this particular type of process; of course, this does not exclude the possibility that the invention may be applicated also to other carbonyl compounds.

European patents 208,311; 267,362; 299,430 and 347,026, in the name of the Applicant, the content of which is incorporated in the present specification, teach that said ammoximation can be effectively obtained in the presence of a catalyst based on silicon and titanium. This type of catalysis permits to obtain very high conversions and selectivities; nevertheless, a quantitative conversion (which would simplify the oxime separation and recovery) is practically never obtained, particularly in the case of cyclohexanone, and the unreacted carbonyl compound represents a problem not only because it is necessary to recover it, but also owing to the possible secondary reactions which it can give rise to (during the separation and the purification of the oxime). The by-products of these reactions (in the case of cyclohexanone, they are cyclohexyl-cyclohexanone, bis-cyclohexenyl-cyclohexanone and octahydro-phenazine) cause, as is known, a worsening of the quality of the caprolactam obtainable in the subsequent Beckmann rearrangement. In order to complete the oximation of the residual ketone, it would be possible to resort to a reaction with a solution of hydroxylamine sulphate, under operative conditions known from the art. The problem of the non-quantitative conversion of the carbonyl compound regards both the ammoximation of cyclohexanone to cyclohexanone-oxime and the ammoximation of other ketones (or alkehydes) such as e.g. acetone, methylethyl ketone (2-butanone), acetophenon, cyclododecanone, enantic aldehyde (1-heptanale), etc. But the hydroxylamine sulphate solutions are obtainable only by complex processes such as, for example, the Rashig process (reduction of the nitrogen oxides with ammonium bisulphite).

The Applicant has now set up an ammoximation process which permits to reduce the amount of residual ketone (or of residual aldehyde), contained in the effluents of the primary steps of the ammoximation process, to the same levels which can be reached with the hydroxylamine sulphate, without resorting, however, to the use of said sulphate, which, as already pointed out, can be produced only by means of a considerably complex process.

In its broadest aspect, the invention relates to a multistep process for the liquid phase ammoximation of carbonyl compounds with $H_2O_2$ and $NH_3$, at 60°–100° C., at 1.5–5 bar and in the presence of a (suspended) catalyst based on silicon, titanium and oxygen, characterized in that:

a) in one or more primary steps the $H_2O_2$: carbonyl compound ratio ranges from 0.9 to 1.15 by mols (preferably from 1.0 to 1.1) and the carbonyl compound conversion is brought at least up to 95% (preferably up to 96–99%);

b) in a last step (exhaustion step) the $H_2O_2$: carbonyl compound ratio is at a higher level, i.e. it ranges from 1.5 to 3.0 by mols (preferably from 1.5 to 2.2).

The above-indicated number ranges are not critical for the purpose of improving the process. The Applicant had previously tried to carry out the quantitative conversion of the carbonyl compound in a single reactor, without any additional completion (exhaustion) step, and using much higher amounts of oxidant ($H_2O_2$) since the beginning, as well as much longer reaction times, but it realized that the initial excess of $H_2O_2$ and the too long times could cause the instability of the reaction system. Namely, competitive reactions were observed, which involved the oxime and/or the carbonyl compound and/or the ammonia; the competitiveness, obviously, refers to the ammoximation reaction. Said competitive (secondary) reactions led to a degradation of the quality of the produced oxime and to a considerable formation of nitrogen-containing by-products ($N_2O$, $N_2$, $NO_2^-$, $NO_3^{31}$ etc.). A consequence of this quality degradation was that the quality specifications of the caprolactam obtainable from the oxime (in cascade) were not met. In other words, it is the Applicant's merit, that it has surprisingly found that it is possible to operate with a high $H_2O_2$ excess, provided said excess is added beyond a certain conversion level, i.e. provided that the residual carbonyl compound concentrations are very low (more exactly: provided that the carbonyl compound conversion has exceeded 95%). In fact it was observed that under these conditions the expected quality worsening did not occur at all and that a practically complete conversion of the carbonyl compound was obtained without carrying out the undersired and complex posttreatments (with hydroxylamine sulphate) and without secondary reactions. The practically quantitative reactions of the carbonyl compound involved by the process according to the invention are namely accompanied by the production of an oxime of equivlanet or higher quality than the one obtainable according to the prior art. A few preferable operative details are briefly listed hereinafter.

A) RESIDUAL REAGENT IN THE EFFLUENT FROM THE PRIMARY STEPS

Really excellent results, in terms of yield calculated on hydrogen peroxide and of quality of the producted oxime, are obtained when the concentration of the residual carbonyl compound in the effluent from the primary steps does not exceed 1% (preferably 0.5%) by weight.

B) OPERATIVE CONDITIONS OF THE PRIMARY STEPS

The ammonia concentration in the liquid reaction medium shall range from 1.0 to 2.5% (preferably from 1.5 to 2.0%) by weight. The $H_2O_2$: ketone (or aldehyde) feed molar ratio shall preferably range, as already mentioned, from 1.0 to 1.1. The concentration of the catalyst suspended in the liquid medium shall be such as to have a specific productivity (expressed as parts by weight of produced oxime per part of catalyst and per hour) from 6 to 12, preferably of about 8. The residence time in each of the primary steps shall not exceed 120 minutes, preferably it shall range from 30 to 90 minutes.

C) EXHAUSTION STEP

In the last step (exhaustion step), where a complete conversion of the residual carbonyl compound shall be reached, in particular a concentration of the unreacted compound not higher than 200 ppm (preferably not higher than 100 ppm and, still more preferably, not higher than 50 ppm on the liquid medium), the above-cited variables, as already mentioned, shall be in the following ranges:

$H_2O_2$: carbonyl compound molar ratio from 1.5 to 3 (preferably from 1.5 to 2.2);

residence time from 10 to 60 minutes.

In the exhaustion step it is better not to introduce further fresh ammonia, since the amount dissolved in the liquid is sufficient for the purpose; a too high ammonia excess, referred to the carbonyl compound, in the presence of a hydrogen peroxide excess would result in an oxidant loss and in the formation of undesired gaseous by-products, such as $N_2$ and $N_2O$. In the exhaustion step, the specific catalyst productivity decreases to a lower level, i.e. from 0.1 to 5 (preferably from 0.3 to 0.5) due to the different operative conditions, and the temperature is preferably maintained at the same value as specificated for the primary steps.

D) GENERAL CONSIDERATIONS

As already mentioned, the temperature in all the steps shall range from 60° to 100° C. (preferably from 70° to 90° C.). At lower temperatures, the reaction kinetics is rather slow, while at higher temperatures the negative effect of the parallel reactions as well as of the consecutive reactions (which start from already formed oxime) begins to become noticeable. The pressure in each of the primary steps and exhaustion step shall prevent the reaction liquid to begin boiling and shall maintain the ammonia concentration in the liquid medium from 1 to 2.5% by weight, preferably at a value lower than 2%; the pressure acts also as motive power in the liquid filtration. Generally, values from 1.5 to 5 bar (preferably from 1.8 to 3 bar) are sufficient, with the values decreasing from the first to the last step. The residence time in each step, with exception of the last, shall be such as to have a residual ketone or residual aldehyde conversion equal to or higher than 95%. The reaction time, in each of these steps, is generally not longer than one hour in order to prevent subsequent reaction of the oxime which has formed. Conversely, too short reaction times lead to an unsatisfactory conversion of the carbonyl compound and to a too high concentration of the reagent in the liquid medium, what promotes the formation of by-products through condensation reactions. In the last step (exhaustion step), the reaction time shall be much shorter in consideration of the lower amount of ketone to be converted. The hydrogen peroxide/ketone feed molar ration in each step, with exception of the exhaustion step, shall preferably be slightly above one, since a little amount of hydrogen peroxide is always consumed, as already mentioned, in parallel reactions (with formation of gaseous products such as $N_2$ and $N_2O$, by ammonia oxidation). Furthermore, as already pointed out, the hydrogen peroxide/ketone molar ratio in the last step, where it is no longer advisable to feed ketone and which shall be capable of bringing the ketone concentration to values lower than 200 and preferably than 100 ppm, shall be considerably higher than the one utilized in the preceding steps (from 1.5 to 3 and preferably from 1.5 to 2.2). The productivity of each step is strictly related to the concentration of the catalyst suspended in the solution contained in each reactor. The continuous feeding to each step shall be regulated in order to have a specific productivity (expressed in parts of produced oxime per part of catalyst and per hour) within the prefixed values. In order to guarantee an effective dispersion of the catalyst in the liquid medium, the catalyst concentration can vary from 1 to 15% by weight. At too low concentrations, the productivity of each step becomes too low and not profitable in the economic respect, while too high concentrations give rise to problems as regards stirring and/or filtration of the reaction product. Preferably and advantageously said concentration can be maintained from 1 to 60% be weight. As a catalyst it is possible to use a titanium silicalite, as is cited for example in European patents 267,362 and 299,430, or one of the amorphous compounds described in European patent 347,926. The average particle size of the catalyst generally ranges from 1 to 100 microns, preferably from 5 to 50 microns.

E) SOLVENTS

Proper solvents for the ammoximation (including the exhaustion step) are the usual organic solvents described in the older patent, a few of which have been cited hereinbefore; said solvents can be water-soluble but also water-insoluble, provided they are stable (under the reaction conditions) to hydrogen peroxide and exhibit a good dissolving power towards the oximes, in particular towards cyclohexanone-oxime. In the case of many oximes it is possible to operate also in an aqueous medium, but cyclohexanone-oxime, owing to its low water-solubility, would ten to deposit onto the catalyst, thereby inhibiting the catalyst activity when the saturation limit is reached. Owing to these reasons it is advantageous to use organic solvents for the purpose of obtaining a high specific productivity of the catalyst and of the reactor. Suitable solvents are, for example, tertiary alcohols, which are stable to hydrogen peroxide, in particular t-butyl alcohol, mixable in any ratios with water, or cyclohexanol, or aromatic compounds such as benzene, toluene, xylenes, chlorobenzene, mixtures thereof, etc. if water-immiscible solvents are utilized, the presence of the following three phases is observed: an aqueous phase (water is produced by the reaction), an organic phase (which maintains in dissolution most of the produced oxime) and a solid phase, which is suspended between the two liquid phases and is composed of the catalytic system. All the examples given later on herein concern the use of t-butyl alcohol as a solvent; however, that does not exclude the possibility of using other solvents which are stable to hydrogen peroxide (either water-soluble or water-insoluble); particularly advantageous results are obtained, for example, by substituting toluene for t-butanol. Due to the low water solubility of cyclohexanone-oxime, it is advisable to limit the water concentration to the one which forms (during the reaction) and to the one which probably must be recycled with the solvent; t-butyl alcohol, for example, which is separated and recycled on concluding of the reaction, has the composition of the aqueous azeotrope (about 12% by weight of water). The oxime concentration in each step is gradually rising and its maximum value, when it is operated in an organic solvent, ranges from 10 to 30%, preferably from 20 to 25% by weight. Although it is economically profitable to operate with an oxime concentration at the maximum values, that is not advisable, as when this concentration exceeds certain values, there is an interference with the consecutive oxime reactions, which lead to the formation of by-products, which very badly affect its quality. The ratio between solvent and carbonyl compound generally ranges from 2.5 to 10 by weight.

F) OPERATIVE DETAILS

Figure 2:
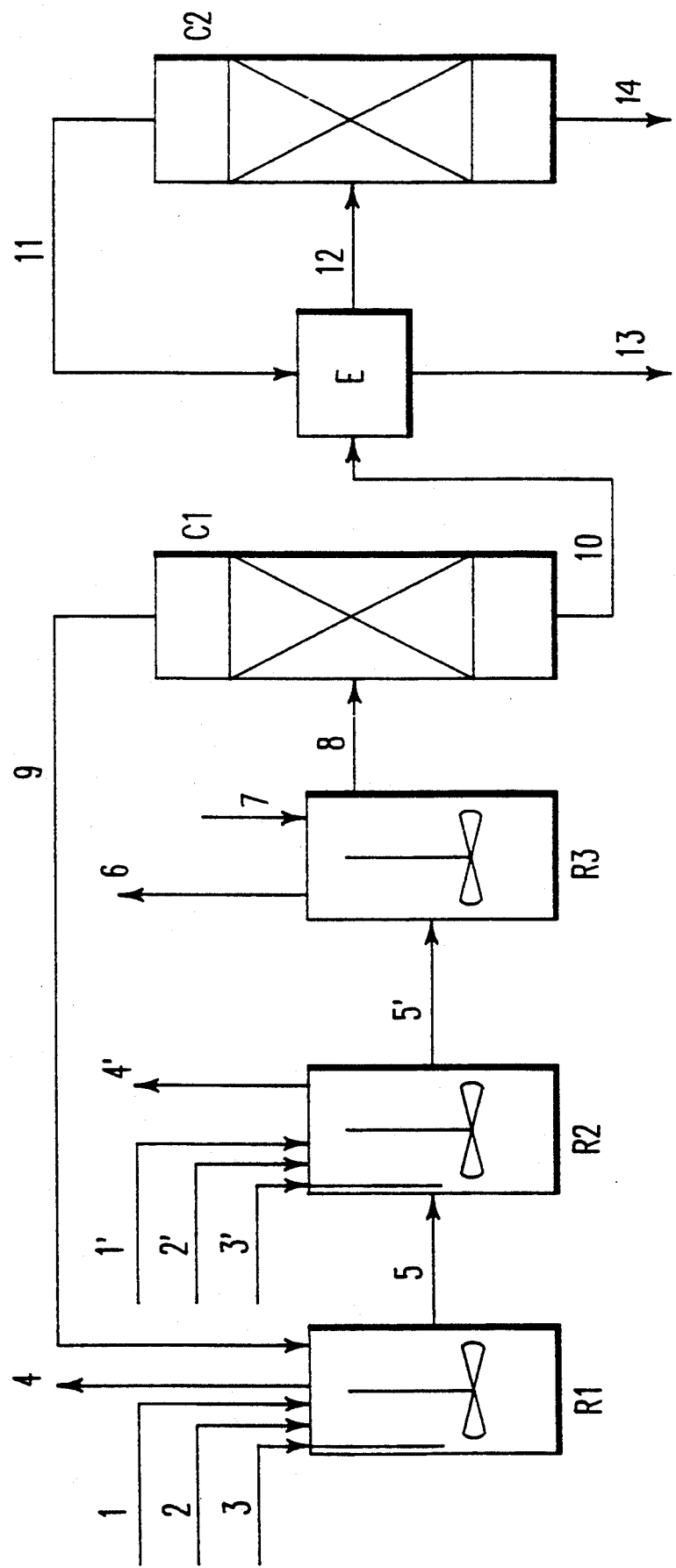

The new process according to the invention and the recovery of the oxime from the solution leaving the last step (exhaustion step), in which the residual carbonyl compound concentration is reduced to a value lower than 200 ppm and even lower than 100 ppm, can be carried out according to the schemes shown in FIG. 1 and in FIG. 2, which are given for merely illustrative purposes, without limiting, however, the scope of the invention.

According to FIG. 1, cyclohexanone (1), hydrogen peroxide (2), ammonia (3) and a t-butanol make-up (not shown in the figure) enter a primary reactor R1, equipped with a stirrer, a filtering element (not shown in the figure) and a vent device (4), where the ammoximation reaction is brought to very high values (up to above 95% of conversion). The reaction mixture (5) flows then into a second step reactor R2 (exhaustion reactor), which too is equipped with a vent (6) and is fed with an excess of hydrogen peroxide (7). The final effluent (8) (practically free from residual ketone and containing t-butanol, cyclohexanone-oxime and ammonia) is sent to a distillation column C1. From the column top, the ammoni and all the solvent (t-butanol in the form of an azeotrope containing 12% by weight of water) are recovered; the ammonia and azeotrope mixture (9) is recycled to the 1st step (primary step). From the bottom of the column, a liquid (1) consisting of water and of cyclohexanone-oxime is recovered and is then subjected to extraction in an apparatus E fed with tolune (11). All the oxime passes to the toluene phase, and from a subsequent separator, not shown in the figure, the toluene phase (12) is withdrawn, which is then sent to a column C2 for the solvent distillation and the oxime dehydration. From said separator (not shown), a water phase (13), containing most of the water-soluble foreign matters, is discharged. From the top of column C2 toluene is recovered in the form of an azeotropic mixture with the reaction water; after a demixing (not shown in the figure), toluene (11) is recycled to the extraction section. The anhydrous oxime (14), which leaves column C2 from the bottom, is sent to the Beckmann rearrangement for the production of caprolactam.

Figure 3:
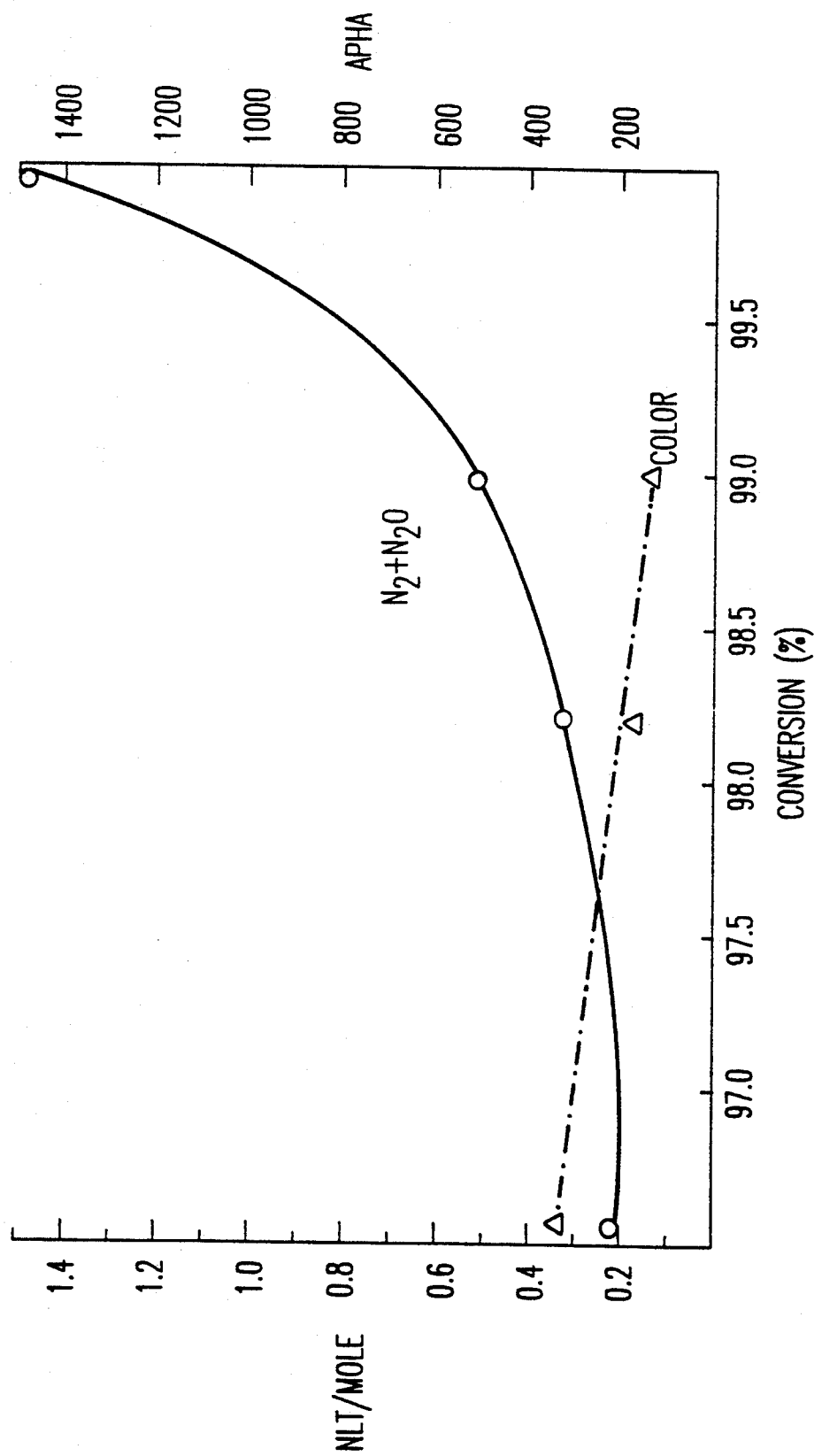
Figure 4:
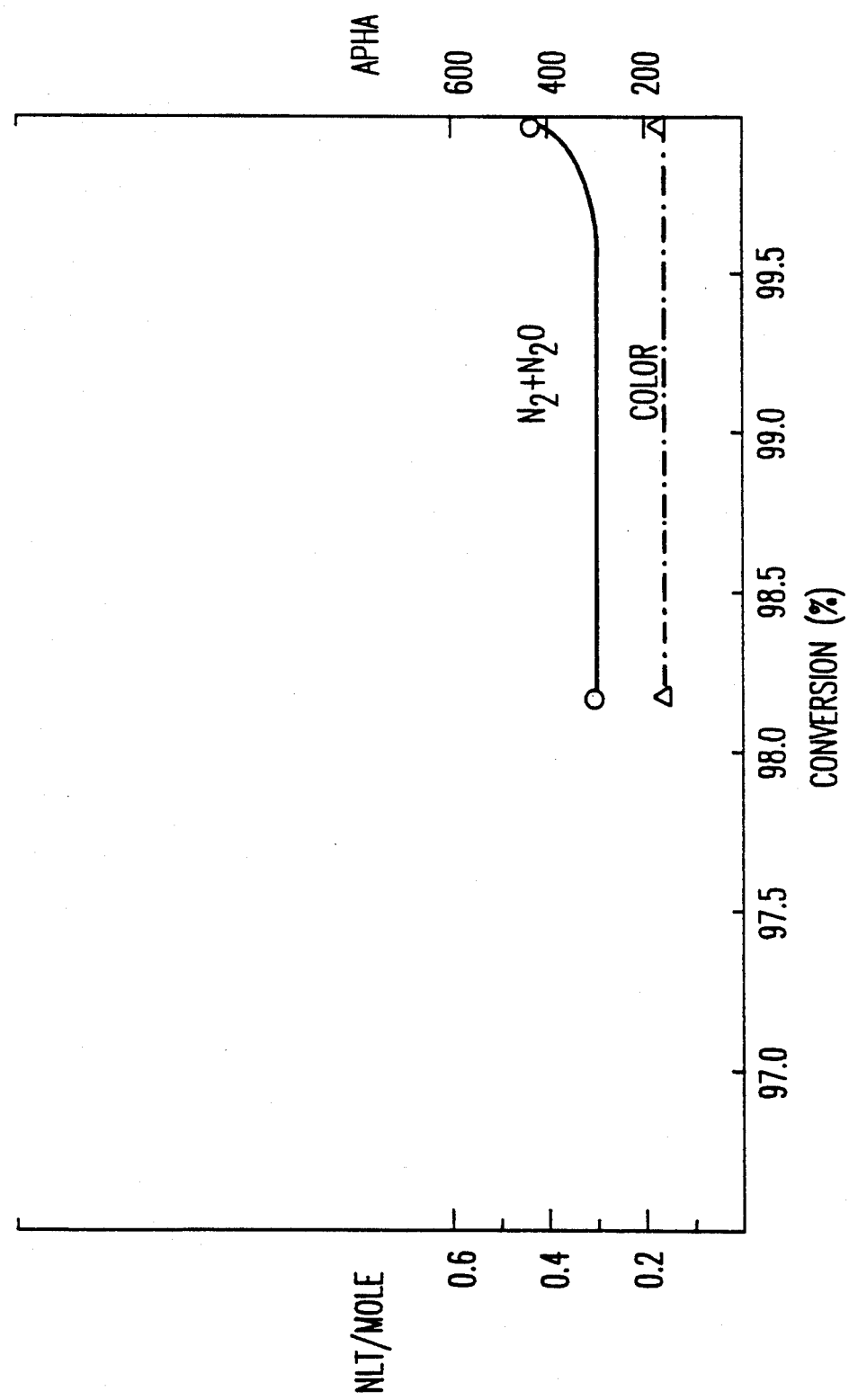

FIG. 2 illustrates, by means of analogous symbols, the case in which, instead of 1 primary step, there are 2 primary steps; FIG. 3 and FIG. 4 concern the results of a few tests and will be discussed in the examples.

G) APPARATUSES

The invention can be advantageously carried into effect in reactors arranged in series and stirred in order to maintain in suspension the catalyst insoluble in the liquid medium. The most suitable reactor is the one which is known as CSTR (Continuous Stirred Tank Reactor). This type of reactor guarantees an effective dispersion of the catalyst system and at the same time, on the basis of a proper regulation of the residence times, the desired conversion of the carbonyl compound, the residual concentration of which shall not exceed certain optimum values, beyond which the already cited formation of undesired by-products takes place (which adversely affect the oxime quality and render the oxime not acceptable for the conversion to caprolactam). Ammonia, hydrogen peroxide and carbonyl compound (in particular cyclohexanone) are continuously fed to each reactor of the primary steps, and the temperature is maintained around the desired value (by means of cooling, since the reaction is exothermic). The reaction heat can be removed indirectly, through a heat exchanger arranged inside the reactor, or by causing the reaction liquid to circulate in a refrigerated circuit outside the reactor (loop reactor). Each reactor shall be equipped with a vent for removing little amounts of gases ($N_2$, $O_2$, $N_2O$), which form as reaction by-products by direct ammonia oxidation. On said vent it is advisable to mount a scrubber for the little amounts of solvent which could be probably entrained by the gaseous compounds. In each reactor it is necessary to install also a filtering system and a purge for the exhausted catalyst. The filtering system, which is arranged inside the reactor or on a circuit outside the reactor, permits to separate the liquid phase from the catalyst, which remains in the reactor, while the filtered liquid is sent to another reactor or to a distillation column (in the case of the last step) for the oxime recovery. It is preferable to install—coupled to the filtering system—a device for the discontinuous purging of exhausted catalyst, which shall be replaced by a fresh catalyst make-up in order to maintain unaltered the catalyst activity in each step. The cyclohexanone feeding, however, is not provided in the last step, since the specific purpose of this step is a complete conversion of the carbonyl compound. Therefore, the reaction liquid flows directly to the oxime recovery section without undergoing further treatments. The (crystalline or amorphous) catalyst particle size, of the order of tens of microns, permits, on one side, an easy dispersion in the reaction medium and, on the other side, an easy separation, by means of the usual filtering systems, from the reaction medium. The following examples are given for merely illustrative purposes and are not to be considered as a limitation of the scope of the invention.

EXAMPLE 1 (COMPARATIVE)—PRIMARY AMMOXIMATION

To a 1 liter reactor, equipped with a stirrer and with continuous feeding and discharged systems, there were continuously fed:

cyclohexanone=70.6 g/h;

t-butyl alcohol (TBA) (containing about 12% by weight of $H_2O$)=232.5 g/h;

hydrogen peroxide (at 49.7% by weight)=54.2 g/h ($H_2O_2$: ketone feeding molar ratio=1.10);

gaseous ammonia=an amount sufficient to maintain a constant concentration (about 2% by weight calculated on the liquid medium).

The level of the liquid was maintained constant by regulating an average residence time of 72 minutes ($+/-1$), and the catalysts concentration was maintained constant around 2% by weight (calculated on the liquid medium). The catalyst consisted of spheroidal titanium silicalite (suspended in the liquid) having an average particle size of about 20 microns. The reaction temperature was maintained constant at 85° C. ($+/-1$) by means of thermostatic fluid circulating in the reactor jacket; the operating pressure was of 2.3 bar. The resulting produce was continuously withdrawn through a stainless steel element equipped with a porous baffle and arranged inside the reactor (dimension of the pores=5 microns), in order to prevent the passage of the catalyst; under regular operating conditions, the product leaving the reactor had the following composition:

| | |
|---|---|
| cyclohexanone-oxime | 21.0% by weight |
| cyclohexanone | 0.3% by weight |
| water | 22.0% by weight |
| ammonia | 2.0% by weight |
| solvent (TBA) | the balance to 100% | what corresponded to the following results:

| | |
|---|---|
| cyclohexanone conversion | 98.3% |
| cyclohexanone selectivity to oxime | 99.6% |
| $H_2O_2$ conversion | 100.0% |
| $H_2O_2$ selectivity to oxime | 89.1% |

Data and results are reported in FIG. 3 and in Table 1, where also the gaseous by-products ($N_2 + N_2O$) and the color (APHA) are indicated. Said APHA coloring can be determined, as is known, according to ASTM-D-1209/69 standards.

EXAMPLE 1/BIS (COMPARATIVE)

Example 1 was repeated, increasing the ($H_2O_2$:ketone) feed molar ration up to a value of 1.15. The results, which are reported in Table 1 and (graphically) in FIG. 3, prove that an increase in the hydrogen peroxide amount involves a little reduction of the product color, while it causes a not allowable increase of the (gaseous) by-products deriving from ammonia oxidation, in particular of $N_2$ and $N_2O$. Conversely, if said ratio is reduced below 1.10, lower amounts of gaseous by-products, but also much higher (APHA) coloring values are obtained, as is shown in FIG. 3, where the by-products amount is expressed as N l./mole (normal) liters per mole of oxime present in the reaction system).

EXAMPLE 2 (COMPARATIVE)—COMPLETION OF AMMOXIMATION WITH HYDROXYLAMINE SULPHATE; INTEGRATED AMMOXIMATION

Example 1 was repeated and the effluent from the reactor was directly fed to an azeotropic distillation column, from the top of which the solvent (t-butanol containing about 12% by weight of $H_2O$) was recovered; from the bottom there was recovered a mixture having the following composition:

| | |
|---|---|
| cyclohexanone-oxime | 58.6% by weight |
| cyclohexanone | 0.85% by weight |
| water | 40.5% by weight |

Said tail mixture was continuously fed to a second (stirred) CSTR reactor, to which there was fed also an aqueous solution of hydroxylamine sulphate of formula $(NH_3OH)_2SO_4$, hereinafter referred to as HYXAS, at a concentration of 10% by weight. The hydroxylamine amount was such as to maintain a $NH_2OH$/cyclohexanone molar ratio equal to 2. The pH was constantly maintained at about 4 (+/−0.1) by adding an ammonia aqueous solution (at 15% by weight). The temperature was maintained at 90° C. (+/−1). The average residence time was of 15 minutes (+/−1), so obtaining a cyclohesanone-oxime having a maximum concentration of residual cyclohexanone lower than 100 ppm. The effluent from the reactor was sent into a phase separator, where (after a residence time sufficient to obtain a sharp phase separation) a cyclohexanone-oxime molten phase, containing 6.5% by weight of water, and a saline aqueous phase were obtained. Said oxime was then dehydrated and sent to the Backmann rearrangement; data and results are reported in Table 1.

EXAMPLE 3

To a first step (primary ammoximation step) there were fed, under the operative conditions of example 1:

| | |
|---|---|
| cyclohexanone | 70.6 g/h |
| TBA (12% of $H_2O$) | 232.5 g/h |
| hydrogen peroxide (49.7%) | 54.2 g/h |
| ($H_2O_2$:ketone feed molar ratio = 1.10) | |
| ammonia: an amount sufficient to maintain a steady concentration (about 2% by weight in the liquid medium). | |

The effluent from this first step, equal to 300 g/h, having the following composition:

| | |
|---|---|
| cyclohexanone-oxime | 21.0% by weight |
| cyclohexanone | 0.30% by weight |
| water | 22.0% by weight |
| ammonia | 2.0% by weight | was fed to a second reactor (exhaustion reactor) similar to the first and maintained at a steady operation pressure of 1.8 bar and at a temperature of 85° C., to which reactor also an aqueous solution of hydrogen peroxide at 50% by weight was fed. The solution amount was equal to 1.6 g/hour, corresponding to a $H_2O_2$/residual ketone molar ratio (exhaustion step) equal to 2.02. Also in this second step (exhaustion step) it was operated with a catalyst in suspension (titanium silicalite) in an amount equal to about 2% by weight of the solution contained in the reactor. The average residence time was of 30 minutes (+/−1). The reaction product leaving the second step (through the filtering element) exhibited the following composition:

| | |
|---|---|
| cyclohexanone-oxime | 21.3% by weight |
| cyclohexanone | less than 100 ppm |
| water | 23.2% by weight |
| ammonia | 1.7% by weight |
| solvent | the balance to 100% |

Considering the globally fed amounts of reagents, the $H_2O_2$/cyclohexanone total molar ratio was equal to 1.13. The cyclohexanone conversion was equal to 99.95%, the selectivity of cyclohexanone to cyclohexanone-oxime was higher than 99%. The hydrogen peroxide conversion was practically quantitative and the selectivity of hydrogen peroxide to oxime was of 87.4%. After separation of the solvent by distillation and after dehydration of the resulting oxime, there was obtained, by Beckmann rearrangement, a caprolactam corresponding (after purification) to the quality characteristics required by the market (optical density, at 290 nanometers, lower than 0.05; permanganate number higher than 20,000 seconds; volatile bases below 0.5 milliequivalents/kg). It is evident that by operating according to the invention it is possible to obtain excellent results without having to utilize a new reagent alien to the ammoximation reaction (for example hydroxylamine sulphate). The very little amount of gaseous by-products (0.41 N l./mole) and the final color (about 180 APHA) are reported as a diagram in FIG. 4, which permits to immediately realize the technical importance of the invention. The crossing point of the two curves in FIG. 3 practically indicates an optimum conversion level, beyond which it is advisable to pass to the exhaustion step (with very high $H_2O_2$: ketone ratios). It was virtually impossible to foresee the range corresponding to the best results (95–99%).

EXAMPLE 4–THREE-STEP PROCESS

The reactor of example 1 was fed with

| | |
|---|---|
| cyclohexanone | 35.3 g/h |
| TBA (12% $H_2O$) | 232.5 g/h |
| hydrogen peroxide (50%) | 25.5 g/h |
| ($H_2O_2$:ketone feed ratio = 1.04) | |
| gaseous ammonia: an amount sufficient to maintain constant its concentration (about 2% by weight calculated on the liquid medium). | |

The liquid level in the reactor was maintained constant and the average residence time was of 60 minutes (+/−1). The catalyst (titanium silicalite) concentration in the reactor was maintained constant (about 2 by weight calculated on the reaction medium). Also the reaction temperature was maintained constant at 85° C. (+/−1) by means of a thermostatic fluid circulating in the reactor jacket; the pressure was equal to 2.8 bar. The cyclohexanone conversion was of 97.8%. The composition of the effluent from the first step was as follows:

| | |
|---|---|
| cyclohexanone-oxime | 13.0% by weight |
| cyclohexanone | 0.26% by weight |
| ammonia | 2.0% by weight |
| water | 18.2% by weight |

The product flowing from this first step passed to a second reactor, identical with the preceding one, and simultaneously there were fed:

| | |
|---|---|
| cyclohexanone | 35.3 g/h |
| hydrogen peroxide (at 50% b.wg.) | 26.0 g/h |
| ($H_2O_2$: ketone feed ratio = 1.06) | |
| gaseous ammonia: an amount sufficient to maintain constant its concentration (about 2% by weight). | |

The operative conditions of the second step were:

| | |
|---|---|
| temperature | 85° C. (+/−1) |
| pressure | 2.3 bar |
| catalyst in suspension | 2% by weight |
| average residence time | 60 minutes (+/−1). |

The effluent from the second step, equal to 373 g/h, had the following composition:

| | |
|---|---|
| cyclohexanone-oxime | 21.4% by weight |
| cyclohexanone | 0.30% by weight |
| ammonia | 2.05% by weight |
| water | 22.1% by weight |

Said effluent (from the second step) was fed to a third reactor (exhaustion reactor), similar to the reactors of the first and second steps, operating under the following conditions;

| | |
|---|---|
| temperature | 85° C. (+/−1) |
| pressure | 1.8 bar |
| concentration of the catalyst in suspension | about 2% by weight |
| averge residence time | 30 minutes. |

Said third reactor was fed with 8 g/h of hydrogen peroxide (at 10% by weight), what was corresponding to an exhaustion ratio equal to 2.06. The product flowing out from the third step, equal to 380 g/h, had the following composition:

| | |
|---|---|
| cyclohexanone-oxime | 21.3% by weight |
| residual cyclohexanone | less than 100 ppm |

The hydrogen peroxide/cyclohexanone total molar ratio was equal to 1.08.

The cyclohexanone conversion was higher than 99.9%.

The cyclohexanone selectivity to cyclohexanone-oxime was of 99.4%.

The hydrogen peroxide conversion was quantitative.

The hydrogen peroxide selectivity to oxime was of 91.7%.

EXAMPLE 5

Under the operative conditions of example 1, a 2-liter reactor was fed with:

| | |
|---|---|
| cyclohexanone | 133.75 g/h |
| t-butyl alcohol (12% $H_2O$) | 491.2 g/h |
| hydrogen peroxide (50% by wg.) | 90 g/h |
| (hydrogen peroxide/ketone feed molar ratio = 0.97) | |
| gaseous ammonia: an amount sufficient to maintain constant the concentration (about 2% by weight on the liquid medium). | |

The effluent, equal to 752 g/h, having the following composition:

| | |
|---|---|
| cyclohexanone-oxime | 19.4% by weight |
| cyclohexanone | 0.9% by weight |
| water | 20.1% by weight |
| ammonia | 2.0% by weight | was fed to an exhaustion reactor of 1-liter volume, operating under the following conditions:

| | |
|---|---|
| temperature | 85° C. |
| pressure | 1.8 bar |
| residence time | 32 minutes |
| suspended catalyst (calculated on the reaction medium) | 2% by weight. |

To the exhaustion reactor there were fed also 44 g/h of hydrogen peroxide at 10% by weight (hydrogen peroxide/ketone molar ratio=1.87). The product leaving the reactor had the following composition:

| | |
|---|---|
| cyclohexanone-oxime | 19.3% by weight |
| cyclohexanone | 200 ppm |
| water | 24.0% by weight |
| ammonia | 1.5% by weight |

The hydrogen peroxide/cyclohexanone total molar ratio was 1.6. The cyclohexanone conversion was higher than 99.9%. The ketone selectivity to oxime was equal to 99.3%. The hydrogen peroxide conversion was quantitative. The hydrogen peroxide selectivity to oxime was equal to 93%.

TABLE 1

| EXAMPLES | ($H_2O_2$/ketone) feed ratio (*) | Oxime (%) | Residual ketone | HYXAS addition | Final ketone | Ketone conversion (%) | $N_2 + N_2O$ (**) | Color (APHA) |
|---|---|---|---|---|---|---|---|---|
| 1 (*) | 1,10 | 21 | 0,30% | no | 0,30% | 98,3 | 0,33 | 180 |
| 1/bis (*) | 1,15 | n.d. | n.d. | no | n.d. | 99,0 | 0,50 | 110 |
| 2 (*) | 1,10 | 21 | 0,85% (**) | yes | less than 100 ppm | n.d. | n.d. | n.d. |

(*) Comparative
(**) After distillation of the solvent
(***) Molar ratio between hydrogen peroxide (100%) and ketone
(****) Normal liters per gram mole of oxime contained in the reaction mixture

TABLE 2

| EXAMPLES | | a Fed ketone (g/h) | c Fed hydrogen peroxide (g/h) | d $H_2O_2$: ketone feed ratio () | e Oxime in the effluent (%) | f Residual ketone in the effluent (%) | g $H_2O_2$: ketone exhaustion () | h Final ketone | i Total ratio (***) |
|---|---|---|---|---|---|---|---|---|---|
| 3 | 1st STEP (primary) | 70,6 | 54,2 | 1,1 | 21,0 | 0,3 | = | = | = |
|   | 2nd STEP (exhaust.) | = | 1,6 | = | 21,3 | | 2,02 | less than 100 ppm | 1,13 |
| 4 | 1st STEP | 35,3 | 25,5 | 1,04 | 13,0 | 0,26 | = | = | = |
|   | 2nd STEP | 35,3 | 26,0 | 1,06 | 21,4 | 0,30 | = | 0,3 | = |
|   | 3rd STEP (exhaust.) | = | 8,0 | = | 21,3 | = | 2,06 | less than 100 ppm | 1,08 |
| 5 | 1st STEP | 133,75 | 90 | 0,97 | 19,4 | 0,9 | = | | |
|   | 2nd STEP (exhaust.) | = | 44 | = | 19,3 | = | 1,87 | 200 ppm | 1,06 |

(**) Molar ratio between hydrogen peroxide (100%) and ketone, which are fed to the same step.
(***) Molar ratio between hydrogen peroxide (100%) and ketone globally fed to all the steps

We claim:

1. A multistep process for the liquid phase ammoximation of carbonyl compounds, wherein said multistep process comprises
   a) in one or more primary steps, reacting a carbonyl compound with $H_2O_2$ and $NH_3$ at 60°–100° C., at 1.5–5.0 bar and in the presence of an effective amount of a catalyst containing silicon, titanium and oxygen wherein the $H_2O_2$ to carbonyl compound molar ratio ranges from 0.9 to 1.15 and the carbonyl compound conversion is carried out at least up to 95%;
   b) in a last step adding additional $H_2O_2$ such that the $H_2O_2$ to carbonyl compound molar ratio ranges from 1.5 to 3.0.

2. The process of claim 1, wherein
   the number of primary steps is selected from 1 and 2 and the catalyst is titanium silicalite;
   the residual carbonyl compound concentration in the effluent from the primary steps is equal to or lower than 1% by weight, and the ammonia concentration in the liquid reaction medium in all the steps ranges from 1.0 to 2.5% by weight;
   the specific productivity in the primary steps ranges from 6 to 12 parts by weight of oxime per part of catalyst and per hour.

3. The process of claim 1, wherein the temperature ranges from 70° to 90° C., the pressure ranges from 1.8 to 4 bar and the catalyst concentration ranges from 1% to 15% by weight.

4. The process of claim 1, wherein the specific productivity in the last step ranges from 0.1 to 5 parts by weight of oxime per parts of catalyst and per hour.

5. The process of claim 1, conducted in the presence of an organic solvent selected from the group consisting of t-butanol and toluene, the ratio between said solvent and said carbonyl compound ranging from 2.5 to 10% by weight.

6. The process of claim 1, wherein the maximum oxime concentration in the liquid reaction medium ranged from 10 to 30% by weight.

7. The process of claim 1, wherein the catalyst particles suspended in the reaction liquid have an average size from 1 to 100 microns.

8. The process of claim 1, wherein the carbonyl compound is selected from the group consisting of cyclohexanone, acetone, methyl ethyl ketone, acetophenone, cyclododecanone and enantic aldehyde.

9. The process of claim 1, wherein oxime is recovered from the reaction liquid by means of an azeotropic distillation, followed by an extraction with organic solvents.

10. The process of claim 1, wherein the reactor for each step is of the CSTR type and is equipped with a porous filtering element, the pores of which have an average size lower than the average size of the catalyst particles.

11. The process of claim 1, wherein in the primary steps the $H_2O_2$: carbonyl compound molar ratio ranges from 1.0 to 1.1 and the carbonyl compound conversion is carried out from 96 to 99%; and in the exhaustion step the $H_2O_2$; carbonyl compound molar ratio ranges from 1.5 to 2.2.

12. The process of claim 2, wherein the residual carbonyl compound concentration in the effluent from the primary steps is equal to or lower than 0.5% by weight, and the ammonia concentration in the liquid reaction media in all the steps ranges from 1.5 to 2.0%.

13. The process of claim 3, wherein the catalyst concentration ranges from 1% to 6% by weight.

14. The process of claim 4, wherein the specific productivity in the last step (exhaustion step) ranges from 0.3 to 0.6 parts by weight of oxime per parts of catalyst and per hour.

15. The process of claim 6, wherein the maximum oxime concentration in the liquid reaction medium ranges from 20 to 25%.

16. The process of claim 7, wherein the catalyst particles suspended in the reaction liquid have an average size of from 5 to 50 microns.

17. The process of claim 9, wherein the oxime is recovered from the reaction liquid (after exhaustion step) by means of an azeotropic distillation followed by an extraction with toluene.

* * * * *